United States Patent [19]

Nubel

[11] Patent Number: 4,788,373

[45] Date of Patent: Nov. 29, 1988

[54] PROCESS FOR ETHYLENE OLIGOMERIZATION TO A PRODUCT RICH IN LINEAR BUTENES USING ZINC-PROMOTED, NICKEL-BASED CATALYST COMPOSITIONS

[75] Inventor: Philip O. Nubel, Naperville, Ill.

[73] Assignee: Amoco Corporation, Chicago, Ill.

[21] Appl. No.: 68,891

[22] Filed: Jun. 30, 1987

[51] Int. Cl.$^4$ ................................................ C07C 2/02
[52] U.S. Cl. .................................... 585/525; 585/510; 585/533
[58] Field of Search .................. 585/510, 525, 533

[56] References Cited

U.S. PATENT DOCUMENTS

| | | | |
|---|---|---|---|
| 2,273,038 | 2/1942 | Houdry et al. | 585/533 |
| 4,451,685 | 5/1984 | Nevitt et al. | 585/510 |
| 4,538,012 | 8/1985 | Miller | 585/255 |

Primary Examiner—Curtis R. Davis
Attorney, Agent, or Firm—Reed F. Riley; William H. Magidson; Ralph C. Medhurst

[57] ABSTRACT

A process for the catalyzed oligomerization of ethylene to a product rich in linear $C_4$ olefins using a catalyst composition made by incorporating a major amount of HAMS-1B crystalline borosilicate molecular sieve composited in an inorganic matrix or an amorphous, silica-alumina support with minor amounts of a nickel compound and a zinc compound and calcining the result to form a composite containing supported zinc and nickel oxides.

10 Claims, No Drawings

PROCESS FOR ETHYLENE OLIGOMERIZATION TO A PRODUCT RICH IN LINEAR BUTENES USING ZINC-PROMOTED, NICKEL-BASED CATALYST COMPOSITIONS

BACKGROUND OF THE INVENTION

This invention relates to an improved process for oligomerizing ethylene using zinc-promoted, nickel-based catalyst compositions and, more particularly, to a process for oligomerizing ethylene to a product rich in linear butenes using a catalyst composition made by incorporating a major amount of (1) a HAMS-1B crystalline borosilicate molecular sieve composited in an inorganic support or (2) an amorphous, high-silica-content, silica-alumina support with minor amounts of a nickel compound and a zinc compound and calcining the result to form a composite containing supported zinc and nickel oxides.

Supported nickel oxide catalysts, such as NiO on silica-alumina supports, have been known as active catalysts for the dimerization of ethylene to butenes since the 1950s. See, for example, U.S. Pat. Nos. 2,381,198; 2,581,228; 2,606,940; 3,341,720; and 4,628,139. Since these catalysts produce significant quantities of $C_5+$ olefins along with butenes, principally hexenes, octenes, decenes and other higher oligomers of ethylene, they are more appropriately termed ethylene oligomerization or dimerization/oligomerization catalysts.

Interest in making linear $C_4$ olefins from ethylene has increased in recent years as a way to utilize ethylene when it is in long supply and also as a way to make 2-butene for alkylation purposes. In addition, since isomerization within the $C_4$ olefin group is well-known, making a linear $C_4$ olefin in good yield is a way to make isobutylene which is useful as an intermediate for t-butyl alcohol and t-butyl methyl ether.

Thus, it is of interest to find catalysts of increased level of activity which are able to convert ethylene more selectively into butenes at higher feed rates, lower reaction pressures or with more dilute ethylene streams and simultaneously minimize production of the higher oligomers.

Now it has been found that by combining a small amount of a zinc compound with a small amount of a nickel compound on a high-silica-content silica-alumina or a supported HAMS-1B crystalline borosilicate molecular sieve, catalyst compositions can be made which show considerably enhanced oligomerization activity while still being reasonably selective in forming linear $C_4$ olefins. This synergistic effect found in mixed nickel-zinc catalyst compositions can be employed to make compositions commercially useful under less severe process conditions.

SUMMARY OF THE INVENTION

Described herein is a process for the oligomerization of ethylene to a product rich in linear butenes comprising contacting ethylene under oligomerization conditions with a catalyst composition comprising a minor amount of nickel oxide and a minor amount of zinc oxide incorporated in a major amount of a support consisting of (1) a HAMS-1B crystalline borosilicate molecular sieve composited in an inorganic matrix, or (2) an amorphous silica-alumina.

DETAILED DESCRIPTION OF THE INVENTION

The ethylene feed to the oligomerization reaction of the instant invention can be a purified ethylene stream or more commonly an impure ethylene stream diluted with one or more other hydrocarbons. Such one or more other hydrocarbons can be saturated hydrocarbons such as ethane, propane, butane and the like and/or minor amounts of unsaturated hydrocarbons such as propene, butenes, pentenes and the like. The exact composition of the feed stream will depend upon the source and the use to which the linear-butene-rich product will be put.

The catalyst compositions of the present invention use nickel and zinc as their oxides incorporated in a support which is either a (1) HAMS-1B crystalline borosilicate molecular sieve, the hydrogen form of the AMS-1B crystalline borosilicate molecular sieve, composited in an inorganic matrix or (2) an amorphous silica-alumina. The preparation and support of such sieves is detailed below. The amorphous silica-aluminas used in the instant invention are well-known in the art and hence need little further discussion. Preferred are silica-aluminas containing more than about thirty (30) weight percent $SiO_2$, and, more preferred are silica-aluminas containing more than about fifty (50) weight percent $SiO_2$. Most preferred are silica-aluminas containing more than about sixty (60) weight percent $SiO_2$.

Incorporated in the support, for example by impregnation, is nickel in the form of the oxide and zinc in the form of the oxide. Such compounds as nickel or zinc nitrate, acetate and other water-soluble salts whose anions decompose on heating are useful for this purpose. The nickel and zinc compounds can be incorporated singly or together, generally using an aqueous solution, and thereafter the incorporated material is heated sufficiently to decompose the compounds yielding nickel and zinc as the oxides. In general, the amount of either zinc and nickel can run between one (1) and about twenty (20) percent by weight, more preferably between about one (1) and about fifteen (15) percent by weight, and, most preferably between about one (1) and about ten (10) weight percent; all percents here are given as weight percent nickel as the oxide or zinc as the oxide.

The $C_4$ olefins comprise 1-butene, 2-butene and isobutene. By linear butenes, which are produced using the catalyst compositions of the instant invention, is meant 1-butene and 2-butene. Only a small quantity of isobutylene is produced by the instant process. In general, the amount of linear butenes in the product is above about thirty (30) weight percent, more preferably, above about forty (40) weight percent, and, most preferably, above about fifty (50) weight percent.

The reaction is desirably carried out in a fixed bed reactor although an ebullated, slurry or fluidized bed or other type of reactor can be useful, too, with appropriate changes in the reactor conditions and possibly the physical makeup of the catalyst as can be understood by one skilled in the art.

The oligomerization is desirably carried out in the temperature range from about 50° C. to about 350° C., more preferably between about 100° C. and about 300° C. Although the reaction can be carried out at atmospheric pressure, elevated pressure from about 10 psig to about 1000 psig, more preferably from about 50 psig to about 700 psig, is desirable. In a fixed bed reactor, the WHSV desirably varies from about 0.1 to about 100, more preferably from about 1 to 10. In other types of reactors, space velocities will be different as may be understood by one skilled in the art.

Some of the catalyst compositions used in this invention are based on AMS-1B crystalline borosilicate molecular sieve, which is described in U.S. Pat. Nos. 4,268,420, 4,269,813, and 4,285,919 and Published European Patent Application No. 68,796, all incorporated herein by reference. AMS-1B crystalline borosilicate generally can be characterized by the X-ray pattern listed in Table A and by the composition formula:

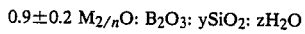

0.9±0.2 $M_{2/n}O$: $B_2O_3$: $ySiO_2$: $zH_2O$ wherein M is at least one cation, n is the valence of the cation, y is between 4 and about 600 and z is between 0 and about 160.

TABLE A

| d-Spacing Å (1) | Assigned Strength (2) |
|---|---|
| 11.2 ± 0.2 | W–VS |
| 10.0 ± 0.2 | W–MS |
| 5.97 ± 0.07 | W–M |
| 3.82 ± 0.05 | VS |
| 3.70 ± 0.05 | MS |
| 3.62 ± 0.05 | M–MS |
| 2.97 ± 0.05 | W–M |
| 1.99 ± 0.05 | VW–M |

(1) Copper K alpha radiation
(2) VS = very weak; W = weak; M = medium; MS = medium strong; VS = very strong The AMS-1B borosilicate molecular sieve useful in this invention can be prepared by crystallizing an aqueous mixture at a controlled pH, of source for cations, an oxide of boron, an oxide of silicon, and an organic template compound.

Typically, the mol ratios of the various reactants can be varied to produce the crystalline borosiicates of this invention. Specifically, the mol ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali or an alkaline earth metal cation or hydrogen. By regulation of the quantity of boron (represented by $B_2O_3$) in the reaction mixture, it is possible to vary the $SiO_2/B_2O_3$ molar ratio in the final product.

More specifically, the material useful in the present invention is prepared by mixing a base, a boron oxide source, and an organic template compound in water (preferably distilled or deionized). The order of addition usually is not critical although a typical procedure is to dissolve base and boric acid in water and then add the template compound. Generally, the silicon oxide compound is added with intensive mixing such as that performed in a Waring Blendor and the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 to about 11.2.

Examples of oxides of silicon useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B crystalline borosilicate include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine as described in Published European Application No. 68,796.

Organic templates useful in preparing AMS-1B crystalline borosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of a silica source such as a silicic acid polymer (Ludox) are added with intensive mixing, preferably the pH is again checked and adjusted to a range of about 11.0±0.2.

Alternatively, AMS-1B crystalline borosilicate molecular sieve can be prepared by crystallizing a mixture of sources for an oxide of silicon, an oxide of boron, an alkyl ammonium compound and ethylenediamine such that the initial reactant molar ratios of water to silica range from about 5 to about 25, preferably about 5 to about 20 and most preferably from about 10 to about 15. In addition, preferably molar ratios for initial reactant silica to oxide of boron range from about 4 to about 150, more preferably from about 5 to about 80 and most preferably from about 5 to about 20. The molar ratio of ethylenediamine to silicon oxide should be above about 0.05, typically below 5, preferably between about 0.1 and about 1.0 and most preferably between about 0.2 and 0.5. The molar ratio of alkylammonium compound, such as tetran-propylammonium bromide, to silicon oxide can range from 0 to about 1 or above, typically above about 0.005, preferably about 0.01 to about 0.1, more preferably about 0.01 to about 0.1 and most preferably about 0.2 to about 0.05.

The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 100° C. to about 250° C., preferably about 125° C. to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° C.–225° C., to form a dry cake which can then be crushed to a powder or to small particles and extruded, pelletized, or made into forms suitable for its intended use. Typically, materials prepared after mild drying contain the organic template compound and water of hydration within the solid mass, and a subsequent activation or calcination procedure is necessary, if it is desired to remove this material from the final product. Typically, mildly dried product is calcined at temperatures ranging from about 260° C. to about 850° C. and preferably about 425° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

The AMS-1B crystalline borosilicate, useful in this invention in its hydrogen form, HAMS-1B, is admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt. % of the total composition. Catalytic compositions can contain about 0.1 wt. % to about 100 wt. % crystalline borosilicate material and preferably contain about 10 wt. % to about 95 wt. % of such material and most preferably contain about 20 wt. % to about 80 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

The following Examples will serve to illustrate certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

The oligomerization results in Example 8 below were performed using a 3-inch Berty autoclave reactor in a continuous flow mode. Catalyst samples (12.12 g each) were charged into a static stainless steel wire basket within the reactor. Catalysts were pretreated in situ with a flow of dry nitrogen at 200° C.–250° C. for several hours prior to the introduction of nitrogen in order to effect complete catalyst composition dehydration. After nitrogen pretreatment, pure ethylene feed was led through the reactor at 1.75 WHSV (based upon total catalyst weight) controlled by a mass flow controller. Reactor pressure was maintained at 350 psig by a back pressure regulator, internal reactor temperature was controlled at 190° C. by an electrical heating jacket and impeller speed was maintained at 1500 RPM. Reactor effluent was analyzed by gas chromatography using a 60 m Durabond DB-1 capillary column made by Alltech Assocs.

Catalyst compositions using both HAMS-1B and silica-alumina were made by the "incipient wetness" technique as follows. After determining the porosity and water uptake of the dried support material by water absorption, a solution of nickel nitrate, zinc nitrate, or a solution of both was made and sufficient solution added to a weighed quantity of sieve or silica-alumina support to be completely absorbed (100% of the pore volume filled) and give the proper percent of nickel, zinc, or both on the support, calculated as the oxide. The material was then calcined in flowing air above about 400° C. to convert the nickel and/or zinc salts to the oxide. All percentages below are given as weight percents.

EXAMPLE 1

HAMS-1B crystalline borosilicate sieve (40% sieve by weight in γ-alumina) in the form of 1/16" extrudate was dried briefly at 200° C. After impregnation with nickel nitrate, the material was dried at 120° C. and subsequently calcined at 450° C. in flowing air for 4 hours. The resulting catalyst contained 5.0% nickel as the oxide.

EXAMPLE 2

The same procedure as in Example 1 was followed except zinc nitrate solution was used. The resulting solid contained 4.0% zinc as the oxide.

EXAMPLE 3

The same procedure as in Example 1 was used except that a mixed solution of both zinc nitrate and nickel nitrate was employed. The resulting solid contained 5.0% nickel as the oxide and 4.0% zinc as the oxide.

EXAMPLE 4

The same procedure as in Example 3 was used. The resulting solid contained 5.0% nickel as the oxide and 2.0% zinc as the oxide.

EXAMPLE 5

The same procedure as in Example 3 was used. The resulting solid contained 5.0% nickel as the oxide and 1.0% zinc as the oxide.

EXAMPLE 6

The same procedure as Example 1 was used except that silica-alumina (United Catalysts, Inc., 1/16" extrudate, 46% SiO$_2$, 295 m$^2$/g) was substituted for the HAMS-1B sieve composited in γ-alumina. The resulting solid contained 5.0% nickel as the oxide.

EXAMPLE 7

The same procedure as Example 3 was used except the silica-alumina (see Example 6) was substituted for the HAMS-1B sieve composited in γ-alumina. The resulting solid contained 5.0% nickel as the oxide and 4.0% zinc as the oxide.

EXAMPLE 8

The procedure under General above was used to obtain the oligomerization data set forth in the Table below.

TABLE

Ethylene Oligomerization at 190° C.

| Example No. | % C$_2$H$_4$ Conversion 3 hrs.[1] | % C$_2$H$_4$ Conversion 1 day[1] | Select. to Lin. Butenes (wt. %) | 2-Butene/ 1-Butene | C$_5$+ Select. (wt. %) |
|---|---|---|---|---|---|
| 1 | 51.3 | 57.6 | 60–55 | 6 | 39–43 |
| 2 | 1.5 | 0.9 | 35–44 | >10 | ~60 |
| 3 | 72.9 | 71.1 | 43–46 | 6 | 53–55 |
| 4 | 81.2 | 76.9 | 39–44 | 6 | 54–60 |
| 5 | 76.9 | 75.2 | 44–49 | 6 | 54–50 |
| 6 | 50.7 | 53.3 | 62 | ~5 | 37 |
| 7 | 80.6 | 69.5 | 47–53 | ~6 | 45–51 |

[1]Time on stream

The results in the Table above show that Example 2 catalyst composition, zinc ion incorporated into HAMS-1B sieve composited in alumina, has a very low ethylene conversion. Further, the results show that Examples 3 and 4 catalyst compositions, where nickel and zinc ions are both incorporated into HAMS-1B sieve composited in alumina, show considerably greater ethylene conversion than would be expected from the results of Example 1 (nickel ion alone) and Example 2 (zinc ion alone) catalyst compositions.

What is claimed is:

1. A process for the oligomerization of ethylene to a product rich in linear butenes comprising contacting ethylene under oligomerization conditions with a catalyst composition comprising a minor amount of nickel as the oxide and a minor amount of zinc as the oxide both incorporated in a major amount of a support consisting of (1) a HAMS-1B crystalline borosilicate molecular sieve composited in an inorganic matrix, or (2) an amorphous silica-alumina.

2. The process of claim 1 wherein said minor amount of each of said nickel as the oxide and said zinc as the oxide runs between about one (1) and about twenty (20) weight percent of said catalyst composition.

3. The process of claim 2 wherein said product contains more than about thirty (30) weight percent of linear butenes based upon the ethylene fed to said process.

4. The process of claim 2 wherein said support is a HAMS-1B crystalline borosilicate molecular sieve composited in alumina, silica-alumina or silica.

5. The process of claim 2 wherein said support is a HAM-1B crystalline borosilicate molecular sieve composited in alumina.

6. The process of claim 5 wherein said product contains more than about thirty (30) weight percent of linear butenes based upon the ethylene fed to said process.

7. The process of claim 5 wherein said HAMS-1B crystalline borosilicate molecular sieve runs between about ten (10) weight percent and about eighty (80) weight percent of said support.

8. The process of claim 7 wherein said product contains more than about thirty (30) weight percent of linear butenes.

9. The process of claim 2 wherein said support is an amorphous silica-alumina containing more than about thirty (30) weight percent SiO$_2$.

10. The process of claim 9 wherein said product contains more than about thirty (30) weight percent of linear butenes.

* * * * *